(12) United States Patent
Damaj

(10) Patent No.: US 11,534,474 B1
(45) Date of Patent: Dec. 27, 2022

(54) ORAL COMPOSITIONS FOR BLADDER REGULATION AND USES THEREOF

(71) Applicant: Aytu Biopharma, Inc., Englewood, CO (US)

(72) Inventor: Bassam Damaj, San Diego, CA (US)

(73) Assignee: AYTU BIOPHARMA, INC., Englewood, CO (US)

( * ) Notice: Subject to any disclaimer, the term of this patent is extended or adjusted under 35 U.S.C. 154(b) by 0 days.

(21) Appl. No.: 17/389,203

(22) Filed: Jul. 29, 2021

(51) Int. Cl.
| | |
|---|---|
| *A61K 36/8945* | (2006.01) |
| *A61K 36/64* | (2006.01) |
| *A61K 36/21* | (2006.01) |
| *A61K 36/40* | (2006.01) |
| *A61K 36/65* | (2006.01) |
| *A61P 13/10* | (2006.01) |
| *A61K 36/68* | (2006.01) |
| *A61K 36/076* | (2006.01) |
| *A61K 36/54* | (2006.01) |
| *A61K 36/67* | (2006.01) |
| *A61K 9/00* | (2006.01) |
| *A61K 36/884* | (2006.01) |

(52) U.S. Cl.
CPC ........ *A61K 36/8945* (2013.01); *A61K 9/0053* (2013.01); *A61K 36/076* (2013.01); *A61K 36/21* (2013.01); *A61K 36/40* (2013.01); *A61K 36/54* (2013.01); *A61K 36/64* (2013.01); *A61K 36/65* (2013.01); *A61K 36/67* (2013.01); *A61K 36/68* (2013.01); *A61K 36/884* (2013.01); *A61P 13/10* (2018.01)

(58) Field of Classification Search
CPC .............. A61K 36/8945; A61K 9/0053; A61K 36/076; A61K 36/21; A61K 36/40; A61K 36/54; A61K 36/64; A61K 36/65; A61K 36/67; A61K 36/68; A61K 36/884; A61P 13/10
See application file for complete search history.

(56) References Cited

FOREIGN PATENT DOCUMENTS

WO    WO-2007086690 A1 *  8/2007  ........... A23L 1/3002

* cited by examiner

*Primary Examiner* — Aaron J Kosar
(74) *Attorney, Agent, or Firm* — Sheridan Ross P.C.

(57) ABSTRACT

Oral compositions for supporting bladder function, reduce frequency of urination, and/or improve or maintain bladder control, suitable for oral administration, are described. Methods of use and uses are described, which include the step of administering an effective amount of the oral compositions to supporting bladder function, reduce frequency of urination, and/or improve or maintain bladder control.

26 Claims, No Drawings

ORAL COMPOSITIONS FOR BLADDER REGULATION AND USES THEREOF

BACKGROUND

Field

The present disclosure generally relates to compositions for improving and/or maintaining bladder function, reducing frequency of urination, and/or increasing bladder control. The present disclosure also generally relates to methods of administering such compositions to improve and/or maintain bladder function, reduce frequency of urination, and/or increase bladder control.

DESCRIPTION OF THE RELATED ART

The circulatory system is responsible for delivering blood, nutrients, and oxygen throughout the body. Many people suffer the effects of poor circulation, which may include acute or chronic numbness in the extremities, coldness in the extremities, and swollen ankles, feet, wrists, hands or fingers. Poor circulation may be attributable to underlying medical conditions such as atherosclerosis and diabetes. Additional causes of poor circulation may the result of other factors such as the effect of certain medications, lack of exercise, smoking, and/or obesity.

Although blood flow in the bladder is not well understood, it is influenced by several mechanical factors such as muscle contraction, compression of urine content, and stretch of tissue layers with bladder distension. Decreased blood flow, caused by increased vascular reactivity, has been postulated to lead to bladder dysfunction in diabetes. In addition, pelvic arterial insufficiency has also been postulated to play an important role in the development of bladder dysfunctions such as detrusor overactivity (DO) and the overactive bladder syndrome.

Diabetic neuropathies are a family of nerve disorders caused by diabetes. People with diabetes can, over the course of the disease, develop nerve damage throughout the body, and nerve problems can occur in every organ system, including the digestive tract, heart, and sex organs. About 60 to 70 percent of people with diabetes have some form of neuropathy, and the neuropathy can cause loss of sensitivity in the feet and hands. Increasing sensitivity of the remaining nerves of neuropathy patients may result in increased sensation, ease the symptoms of neuropathy, and greatly improve a person's quality of life.

Frequent urination refers to a more-often-than-regular urge to urinate, and is sometimes simply referred to as frequency. In severe cases, it may be referred to as polyuria. It can be caused by various underlying medical conditions such as kidney disease, ureter dysfunction, diabetes mellitus, diabetes insipidus, and/or prostrate dysfunction.

Lack of bladder control, also known as urinary incontinence, may be temporary or persistent. Multiple underlying physical problems or changes may cause persistent urinary incontinence, such as aging, enlarged prostate, prostate cancer, obstructions, or neurological disorders. As such, urinary symptoms can arise due to neurological disease in the brain, the suprasacral spinal cord, the sacral spinal cord, or the peripheral nervous system. Multiple sclerosis, Parkinson's disease, a stroke, a brain tumor, or a spinal injury can interfere with nerve signals involved in bladder control, causing urinary incontinence.

Based on the above, there exists a need for composition and methods for improving and maintaining bladder function, for reducing frequency of urination (and/or reducing the frequency of the urge to urinate), and for maintaining bladder control.

SUMMARY

An oral composition is provided comprising at least one of each of the following extracts: *Rehmanniae radix* root extract; *Achyranthis radix* root extract; *Corni Officinalis* fruit extract; *Paeonis Suffruticosa* rootbark extract; *Alisma rhizoma* extract; *Dioscorea Villosa* (Wild Yam) *rhizoma* extract; *Plantaginis semen* seed extract; *Poria Cocos* (hoelen) fruiting body extract; Cinnamon cortex bark extract; and *Piper nigrum* fruit extract.

The oral composition may be formulated as a capsule. In some embodiments, the capsule may comprise from about 75 mg to about 175 mg, or from about 100 mg to about 150 mg, or about 125 mg *Rehmanniae radix* root extract. In some embodiments, the capsule may comprise from about 25 mg to 125 mg, or from about 50 mg to about 100 mg, or about 75 mg *Achyranthis radix* root extract. In some embodiments, the capsule may comprise from about 25 mg to 125 mg, or from about 50 mg to about 100 mg, or about 75 mg *Corni Officinalis* fruit extract. In some embodiments, the capsule may comprise from about 25 mg to 125 mg, or from about 50 mg to about 100 mg, or about 75 mg *Paeonis Suffruticosa* root bark extract. In some embodiments, the capsule may comprise from about 25 mg to 125 mg, or from about 50 mg to about 100 mg, or about 75 mg *Alisma rhizoma* rhizome extract. In some embodiments, the capsule may comprise from about 25 mg to 125 mg, or from about 50 mg to about 100 mg, or about 75 mg *Dioscorea Villosa rhizoma* extract. In some embodiments, the capsule may comprise from about 25 mg to 125 mg, or from about 50 mg to about 100 mg, or about 75 mg *Plantaginis semen* seed extract. In some embodiments, the capsule may comprise from about 25 mg to 125 mg, or from about 50 mg to about 100 mg, or about 75 mg hoelen fruiting body extract. In some embodiments, the capsule may comprise from about 1 mg to 75 mg, or from about 5 mg to about 50 mg, or about 25 mg Cinnamon cortex bark extract. In some embodiments, the capsule may comprise from about 0.1 mg to about 15 mg, or from about 1 mg to about 10 mg, or about 5 mg *Piper nigrum* fruit extract. *Piper nigrum* fruit extract is commercially available as, and in preferred embodiments is, BioPerine®. BioPerine® is a registered trademark of Sabinsa Corporation.

In some embodiments, the compositions disclosed herein may further comprise one or more pharmaceutically acceptable excipients or carriers. These optional excipients are preferably selected from the group consisting of gelatin, silicon dioxide, vegetable fiber, rice flour, magnesium stearate, maltodextrin, microcrystalline cellulose, and combinations thereof.

In some embodiments, the oral composition is substantially free of processed Aconiti tuber.

The oral composition may be administered one, two, three, or four times a day. Each dosage may involve the administration of one or two capsules. The composition may be administered over a period of at least one month, at least two months, or at least ten, twelve, or fourteen weeks. In a preferred embodiment, the oral composition is administered three times per day, consistently, over a period of at least twelve (12) weeks.

In some embodiments, the compositions disclosed herein may be used in improving circulation. Another embodiment is a method of improving the function of the urinary system and/or increasing circulation by administering a composition comprising one or more of the group consisting of *Rehmanniae radix* extract; *Achyranthis radix* extract; *Corni Officinalis* extract; *Paeonis Suffruticosa* extract; *Alisma rhizoma* extract; *Dioscorea villosa rhizoma* extract; *Plantaginis semen* extract; *hoelen* extract; Cinnamon cortex extract; and *Piper nigrum* extract.

In some embodiments, the compositions disclosed herein may be used in increasing nerve sensation. Another embodiment is a method of improving the function of the urinary system and/or increasing nerve sensation by administering a composition comprising one or more of the group consisting of *Rehmanniae radix* extract; *Achyranthis radix* extract; *Corni Officinalis* extract; *Paeonis Suffruticosa* extract; *Alisma rhizoma* extract; *Dioscorea Villosa rhizoma* extract; *Plantaginis semen* extract; *hoelen* extract; Cinnamon cortex extract; and *Piper nigrum* extract.

The subject being treated may experience bladder dysfunction, frequency of urination, frequency of the urge to urinate, lack of bladder control, and combinations thereof. The subject may experience one or more of these conditions temporarily, persistently, or chronically, or in a combination thereof. The subject may be identified by analyzing the results of a questionnaire completed prior to treatment, and the effect of the disclosed formulation, administered according to the course of treatment, to reduce bladder dysfunction, maintain bladder function, reduce the frequency of urination, reduce frequency of the urge to urinate, and/or avoid the lack of bladder control may be determined by analyzing the results of a questionnaire complete after a course of treatment.

DETAILED DESCRIPTION OF THE PREFERRED EMBODIMENT

In some embodiments, an oral composition is provided comprising *Rehmanniae radix* extract, which is a perennial herb belonging to the Scrophulariaceae family. The composition may also comprise at least one of the following: *Achyranthis radix* extract; *Corni Officinalis* extract; *Paeonis Suffruticosa* extract; *Alisma rhizoma* extract; *Dioscorea Villosa rhizoma* extract; *Plantaginis semen* extract; *hoelen* extract; Cinnamon cortex extract; and *Piper nigrum* extract. In some embodiments, the oral composition may further include one or more excipients including, but not limited to, gelatin, silicon dioxide, vegetable fiber, rice flour, magnesium stearate, maltodextrin, and microcrystalline cellulose. In some embodiments, the oral composition is substantially free of processed Aconiti tuber.

In some embodiments, the compositions provided herein include *Rehmanniae radix* extract. *Rehmanniae radix* extract is used to remove extravasated blood and increase body fluid and is also used for breaking fevers, cardiac stimulation, and detoxification. In some embodiments, the amount of *Rehmanniae radix* extract in the oral composition may be, for example, at least about 4 wt. %, at least about 9 wt. %, at least about 14 wt. %, at least about 15 wt. %, at least about 16 wt. %, at least about 17 wt. %, at least about 18 wt. %, at least about 19 wt. %, at least about 20 wt. %, at least about 21 wt. %, at least about 22 wt. %, at least about 23 wt. %, at least about 24 wt. %, at least about 29 wt. %, at least about 34 wt. %, or within a range defined by any two of the aforementioned concentrations. For example, in some embodiments, the amount of *Rehmanniae radix* extract present in the oral composition will range from, for example, approximately 15 wt. % to approximately 22 wt. %, from approximately 16 wt. % to approximately 21 wt. %, from approximately 17 wt. % to approximately 20 wt. %, or from approximately 18 wt. % to approximately 19 wt. %.

In some embodiments, the compositions provided herein include *Achyranthis radix* extract. *Achyranthis radix* extract has been considered to be beneficial for health and contains compounds which function to tonifying the liver and kidney and strengthen tendons and bones. Without being bout to any particular theory, regular ingestion of *Achyranthis radix* extract may promote circulation and treat amenorrhea, abdominal mass, headache and dizziness. In some embodiments, the amount of *Achyranthis radix* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Achyranthis radix* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *Corni Officinalis* extract. *Corni Officinalis* extract exhibits extensive pharmacological activities including hypoglycemic, antioxidant, anti-inflammatory, anticancer, neuroprotective, hepatoprotective, and nephroprotective activities. In some embodiments, the amount of *Corni Officinalis* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Corni Officinalis* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *Paeonis Suffruticosa* extract. *Paeonis Suffruticosa* extract promotes blood circulation and removes blood stasis. It has been used as an analgesic, antispasmodic, antiaggregatory, and antioxidative agent. In some embodiments, the amount of *Paeonis Suffruticosa* extract in the oral composition may be, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Paeonis Suffruticosa* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *Alisma rhizoma* extract. *Alisma rhizoma* extract has been used to treat dysuria, edema, nephropathy, hyperlipidemia, and diabetes. *Alisma rhizoma* extract also possess a wide spectrum of pharmacological effects, such as diuretic, antimetabolic disorder, hepatoprotective, immunomodulatory, antiosteoporotic, anti-inflammatory, antitumor, antibacterial, and antiviral activities. In some embodiments, the amount of *Alisma rhizoma* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Alisma rhizoma* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *Dioscorea Villosa rhizoma* extract. *Dioscorea Villosa rhizoma* extract has been used to decreases damage in renal tubules, inflammation in the central vein, and necrosis in the liver. *Dioscorea Villosa rhizoma* extract is also known as an anti-inflammatory agent. In some embodiments, the amount of *Dioscorea Villosa rhizoma* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Dioscorea Villosa rhizoma* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *Plantaginis semen* extract. *Plantaginis semen* extract has been used to treat blurred vision. *Plantaginis semen* extract may also be used to reduce hyperglycemia. In some embodiments, the amount of *Plantaginis semen* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *Plantaginis semen* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include *hoelen* extract. *hoelen* extract has been used to treat nausea, vomiting, diarrhea, loss of appetite, stomachache, and stomach ulcer. *hoelen* extract also possess diuretic, anti-inflammatory, sedative, and tonic effects. In some embodiments, the amount of *hoelen* extract in the oral composition may be, for example, at least about 1 wt. %, at least about 6 wt. %, at least about 7 wt. %, at least about 8 wt. %, at least about 9 wt. %, at least about 10 wt. %, at least about 11 wt. %, at least about 12 wt. %, at least about 13 wt. %, at least about 14 wt. %, at least about 15 wt. %, at least about 16 wt. %, at least about 21 wt. %, at least about 26 wt. %, or within a range defined by any two of the aforementioned concentrations. For example, in some embodiments, the amount of *hoelen* extract present in the oral composition will range from, for example, approximately 7 wt. % to approximately 14 wt. %, from approximately 8 wt. % to approximately 13 wt. %, from approximately 9 wt. % to approximately 12 wt. %, or from approximately 10 wt. % to approximately 11 wt. %.

In some embodiments, the compositions provided herein include Cinnamon cortex extract. Cinnamon cortex extract has been used to improve blood circulation. Cinnamon cortex extract also has wide varieties of pharmacological actions such as anti-inflammatory action and anti-platelet aggregation. In some embodiments, the amount of Cinnamon cortex extract in the oral composition may be, for example, at least about 0.1 wt. %, at least about 1 wt. %, at least about 2 wt. %, at least about 3 wt. %, at least about 4 wt. %, at least about 5 wt. %, at least about 6 wt. %, at least about 7 wt. %, at least about 8 wt. %, at least about 9 wt. %, at least about 10 wt. %, at least about 19 wt. %, or within a range defined by any two of the aforementioned concentrations. For example, in some embodiments, the amount of Cinnamon cortex extract present in the oral composition will range from, for example, approximately 0.1 wt. % to approximately 7 wt. %, from approximately 1 wt. % to approximately 6 wt. %, from approximately 2 wt. % to approximately 5 wt. %, or from approximately 3 wt. % to approximately 4 wt. %.

In some embodiments, the compositions provided herein include *Piper nigrum* extract. *Piper nigrum* extract is commercially available as, and in preferred embodiments is, BioPerine®. *Piper nigrum* extract is an extract obtained from black pepper fruits (*Piper nigrum*). Black pepper extract is thought to increase the bioavailability of certain nutritional compounds. In some embodiments, the amount of *Piper nigrum* extract in the oral composition may be, for example, at least about 0.001 wt. %, at least about 0.01 wt. %, at least about 0.1 wt. %, at least about 0.5 wt. %, at least about 0.7 wt. %, at least about 1 wt. %, at least about 2 wt. %, at least about 3 wt. %, at least about 4 wt. %, at least about 5 wt. %, at least about 10 wt. %, or within a range defined by any two of the aforementioned concentrations. For example, in some embodiments, the amount of *Piper nigrum* extract present in the oral composition will range from, for example, from approximately 0.001 wt. % to approximately 3 wt. %, from approximately 0.01 wt. % to approximately 2 wt. %, or from approximately 0.1 wt. % to approximately 1 wt. %.

In some embodiments, a method is provided for promoting bladder function. The method comprises the steps of: (i) identifying a subject in need of promoting bladder function; (ii) administering a therapeutically effective amount of an oral formulation disclosed herein to the subject; and thereby (iii) promoting bladder function in the subject.

In other embodiments, a method is provided for supporting bladder function. The method may comprise the steps of: (i) identifying a subject in need of supporting bladder function; (ii) administering a therapeutically effective amount of an oral formulation disclosed herein to the subject; and thereby (iii) supporting bladder function in the subject.

In other embodiments, method is provided for reducing frequency of urination. The method comprises the steps of: (i) identifying a subject in need of reducing frequency of urination; (ii) administering a therapeutically effective amount of an oral formulation disclosed herein to the subject; and thereby (iii) reducing frequency of urination in the subject.

In other embodiments, a method is provided for maintaining bladder control. The method comprises the steps of: (i) identifying a subject in need of maintaining bladder control; (ii) administering a therapeutically effective amount of an oral formulation disclosed herein to the subject; and thereby (iii) maintaining bladder control in the subject.

In some embodiments, the subject can be identified through the use of a questionnaire. For example, potential subjects are asked to provide responses to questions related to their age, genetic and/or medical histories, present symptoms and severity thereof, current medications. In some embodiments, the subject self-identifies and experiencing one or more conditions selected from poor bladder function, bladder dysfunction, frequency of urination, lack of bladder control. The subject completes the questionnaire before administering the oral composition, optionally during a course of administration of the oral composition, and after a course of administration of the oral composition. The results of the questionnaire indicate that the administration of the oral composition leads to an improved assessment of bladder function, frequency of urination, and/or bladder control, and combinations thereof.

In some embodiments, the oral composition is administered once per day, two times per day, three times per day, or four times per day, preferably two times per day. In some embodiments, the compounds will be administered for a period of continuous therapy, for example for one day, for two days, for three days, for a week, for two weeks, for one month, for two months, for three months, for four months, for five months, for six months, seven months, for eight months, for nine months, for ten months, for eleven months, for twelve months, for eighteen months, for two years, for three years, for four years, or for five or more years.

In some embodiments, the oral compositions disclosed herein may formulated into an oral dosage form. In some embodiments, the oral dosage form may be a capsule. In some embodiments, the capsule may comprise from about 75 mg to about 175 mg, or from about 100 mg to about 150 mg, or about 125 mg *Rehmanniae radix* extract. In some embodiments, the capsule may comprise from about 25 mg to 125 mg, or from about 50 mg to about 100 mg, or about 75 mg *Achyranthis radix* extract. In some embodiments, the capsule may comprise from about 25 mg to 125 mg, or from about 50 mg to about 100 mg, or about 75 mg *Corni Officinalis* extract. In some embodiments, the capsule may comprise from about 25 mg to 125 mg, or from about 50 mg to about 100 mg, or about 75 mg *Paeonis Suffruticosa* extract. In some embodiments, the capsule may comprise from about 25 mg to 125 mg, or from about 50 mg to about 100 mg, or about 75 mg *Alisma rhizoma* extract. In some embodiments, the capsule may comprise from about 25 mg to 125 mg, or from about 50 mg to about 100 mg, or about 75 mg *Dioscorea Villosa rhizoma* extract. In some embodiments, the capsule may comprise from about 25 mg to 125 mg, or from about 50 mg to about 100 mg, or about 75 mg *Plantaginis semen* extract. In some embodiments, the capsule may comprise from about 25 mg to 125 mg, or from about 50 mg to about 100 mg, or about 75 mg *hoelen* extract. In some embodiments, the capsule may comprise from about 1 mg to 75 mg, or from about 5 mg to about 50 mg, or about 25 mg Cinnamon cortex extract. In some embodiments, the capsule may comprise from about 0.1 mg to about 15 mg, or from about 1 mg to about 10 mg, or about 5 mg *Piper nigrum* extract.

In some embodiments, the compositions disclosed herein may further comprise one or more pharmaceutically acceptable excipients or carriers. In some embodiments, the oral composition disclosed herein may comprise an excipient selected from gelatin, silicon dioxide, vegetable fiber, rice flour, magnesium stearate, maltodextrin, microcrystalline cellulose, and combinations thereof.

In some embodiments, the oral composition is substantially free of processed Aconiti tuber.

In some embodiments, the dose administered to the subject may be one, two, three, four, or more capsules. In some embodiments each dose may comprise two capsules. In some embodiments, four capsules are administered to the subject per day.

The terms "pharmaceutically acceptable carrier" and "pharmaceutically acceptable excipient," as used herein, include any and all pharmaceutically-acceptable solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

The term "excipient," as used herein, refers to an inert or relatively inert substance that is added to a pharmaceutical composition to impart certain properties to the composition including, without limitation, improved or desired bulk, consistency, stability, binding ability, lubrication, disintegrating ability, etc. A "diluent" is a type of excipient.

EXAMPLES

Example 1

Materials used in preparing the oral compositions described herein may be made by known methods or are commercially available. It is also possible to make use of variants which are themselves known to those of ordinary skill in this art, but are not mentioned in greater detail. The skilled artisan given the literature and this disclosure is well equipped to prepare the formulations of the instant application.

Representative oral compositions are shown in Table 1 below, with the amounts for "broad," "intermediate," and "preferred" ranges.

TABLE 1

| Component | Broad Ranges (mg) | Intermediate Ranges (mg) | Preferred Amounts (mg) |
|---|---|---|---|
| Rehmanniae Radix extract | 75-175 | 100-150 | 125 |
| Achyranthis Radix extract | 25-125 | 50-100 | 75 |
| Corni Officinalis extract | 25-125 | 50-100 | 75 |
| Paeonis Suffruticosa extract | 25-125 | 50-100 | 75 |
| Alisma rhizoma extract | 25-125 | 50-100 | 75 |
| Dioscorea Villosa rhizoma extract | 25-125 | 50-100 | 75 |
| Plantaginis semen extract | 25-125 | 50-100 | 75 |
| Hoelen extract | 25-125 | 50-100 | 75 |
| Cinnamon cortex extract | 1-75 | 5-50 | 25 |
| Piper nigrum extract | 0.1-15 | 1-10 | 5 |
| Total | 251.1-1140 | 456-910 | 680 |

Example 2

Subjects over the age of 40, in need of therapy for bladder regulation, are identified through a multi-part questionnaire. Subjects provide information age, weight, height, and indicated whether they suffered from bladder dysfunction, and underlying medical conditions including diabetes. Subjects are also asked about whether they suffered from frequent urination or lack of bladder control, and to rate the discomfort owning to bladder dysfunction on a scale of 1 to 10, with 1 being no bother and 10 being severe discomfort.

Subjects are administered three (3) capsules, daily, each containing the preferred formulation of Example 1, with meals, for a period of at least twelve (12) weeks. Subjects are then provided with a questionnaire to confirm that the administration was substantial consistent, at three (3) times per day over a period of at least twelve (12) weeks, and to self-assess their symptoms, and their severity, as compared to their initial assessments.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

What is claimed is:

1. An oral composition for use in bladder regulation and/or improving circulation, the composition comprising: Rehmanniae radix extract; Achyranthis radix extract; Corni officinalis extract; Paeonis suffruticosa extract; Alisma rhizoma extract; Dioscorea villosa rhizoma extract; Plantaginis semen extract; hoelen extract; cinnamon cortex extract; and Piper nigrum extract.

2. The composition of claim 1, wherein the composition comprises: from about 10 to about 25 wt % Rehmanniae radix extract; from about 5 to about 20 wt % Achyranthis radix extract; from about 5 to about 20 wt % Corni officinalis extract; from about 5 to about 20 wt % Paeonis suffruticosa extract; from about 5 to about 20 wt % Alisma rhizoma extract; from about 5 to about 20 wt % Dioscorea villosa rhizoma extract; from about 5 to about 20 wt % Plantaginis semen extract; from about 5 to about 20 wt % hoelen extract; from about 0.1 to about 7 wt % cinnamon cortex extract; and from about 0.001 to about 3 wt % Piper nigrum extract.

3. The composition of claim 2, wherein the composition comprises: from about 15 to about 22 wt % Rehmanniae radix extract; from about 7 to about 14 wt % Achyranthis radix extract; from about 7 to about 14 wt % Corni officinalis extract; from about 7 to about 14 wt % Paeonis suffruticosa extract; from about 7 to about 14 wt % Alisma rhizoma extract; from about 7 to about 14 wt % Dioscorea villosa rhizoma extract; from about 7 to about 14 wt % Plantaginis semen extract; from about 7 to about 14 wt % hoelen extract; from about 1 to about 6 wt % cinnamon cortex extract; and from about 0.01 to about 2 wt % Piper nigrum extract.

4. The composition of claim 3, wherein the composition comprises: about 18 wt % Rehmanniae radix extract; about 11 wt % Achyranthis radix extract; about 11 wt % Corni officinalis extract; about 11 wt % Paeonis suffruticosa extract; about 11 wt % Alisma rhizoma extract; about 11 wt % Dioscorea villosa rhizoma extract; about 11 wt % Plantaginis semen extract; about 11 wt % hoelen extract; about 4 wt % cinnamon cortex extract; and about 1 wt % Piper nigrum extract.

5. The composition of claim 1, wherein the composition consists essentially of: Rehmanniae radix extract; Achyranthis radix extract; Corni officinalis extract; Paeonis suffruticosa extract; Alisma rhizoma extract; Dioscorea villosa rhizoma extract; Plantaginis semen extract; hoelen extract; cinnamon cortex extract; and Piper nigrum extract.

6. The composition of claim 1, further comprising one or more pharmaceutically acceptable excipients.

7. The composition of claim 6, wherein the pharmaceutically acceptable excipient is selected from the group consisting of gelatin, silicon dioxide, vegetable fiber, rice flour, magnesium stearate, maltodextrin, microcrystalline cellulose, and combinations thereof.

8. An oral composition for use in reducing frequency of urination, the composition consisting essentially of:
    100-150 mg Rehmanniae radix extract;
    50-100 mg Achyranthis radix extract;
    50-100 mg Corni officinalis extract;
    50-100 mg Paeonis suffruticosa extract;
    50-100 mg Alisma rhizoma extract;
    50-100 mg Dioscorea villosa rhizoma extract;
    50-100 mg Plantaginis semen extract;
    50-100 mg hoelen extract;
    5-50 mg cinnamon cortex extract; and
    1-10 mg Piper nigrum extract.

9. An oral composition for use in reducing frequency of urination the composition consisting essentially of:
    125 mg Rehmanniae radix extract;
    75 mg Achyranthis radix extract;
    75 mg Corni officinalis extract;
    75 mg Paeonis suffruticosa extract;
    75 mg Alisma rhizoma extract;
    75 mg Dioscorea villosa rhizoma extract;
    75 mg Plantaginis semen extract;
    75 mg hoelen extract;
    25 mg cinnamon cortex extract; and
    5 mg Piper nigrum extract.

10. An oral composition for use in supporting bladder function, the composition consisting essentially of:
    100-150 mg Rehmanniae radix extract;
    50-100 mg Achyranthis radix extract;
    50-100 mg Corni officinalis extract;
    50-100 mg Paeonis suffruticosa extract;
    50-100 mg Alisma rhizoma extract;
    50-100 mg Dioscorea villosa rhizoma extract;
    50-100 mg Plantaginis semen extract;

50-100 mg *hoelen* extract;
5-50 mg cinnamon cortex extract; and
1-10 mg *Piper nigrum* extract.

11. An oral composition for use in supporting bladder function, the composition consisting essentially of:
125 mg *Rehmanniae radix* extract;
75 mg *Achyranthis radix* extract;
75 mg *Corni officinalis* extract;
75 mg *Paeonis suffruticosa* extract;
75 mg *Alisma rhizoma* extract;
75 mg *Dioscorea villosa rhizoma* extract;
75 mg *Plantaginis semen* extract;
75 mg *hoelen* extract;
25 mg cinnamon cortex extract; and
5 mg *Piper nigrum* extract.

12. The composition of any one of claims 1-9, wherein the oral composition is substantially free of an *Aconiti tuber* extract.

13. A method of improving bladder control in a subject comprising administering an effective amount of a composition of any one of claim 1-7, 8, or 9 to the subject, where the subject is in need of improved circulation.

14. The method of claim 13, wherein the subject is a human.

15. The method of claim 13, wherein the administration is three times per day.

16. The method of claim 13, where the administration is for a period of at least twelve weeks.

17. A method of treating a bladder dysfunction in a subject comprising the step of administering an effective amount of a composition any one of claims 1-9 to the subject, wherein the subject is in need of treatment for a bladder dysfunction.

18. The method of claim 17, wherein the subject is a human.

19. The method of claim 17, wherein the administration is three times per day.

20. The method of claim 17, where the administration is for a period of at least twelve weeks.

21. A method improving bladder function comprising administering an effective amount of the composition of the claim 12.

22. The method of claim 21, wherein the subject is a human.

23. The method of claim 21, wherein the administration is three times per day.

24. The method of claim 21, where the administration is for a period of at least twelve weeks.

25. An oral composition for use in improving circulation, the composition consisting essentially of:
100-150 mg *Rehmanniae radix* extract;
50-100 mg *Achyranthis radix* extract;
50-100 mg *Corni officinalis* extract;
50-100 mg *Paeonis suffruticosa* extract;
50-100 mg *Alisma rhizoma* extract;
50-100 mg *Dioscorea villosa rhizoma* extract;
50-100 mg *Plantaginis semen* extract;
50-100 mg *hoelen* extract;
5-50 mg cinnamon cortex extract; and
1-10 mg *Piper nigrum* extract.

26. An oral composition for use in improving circulation, the composition consisting essentially of:
125 mg *Rehmanniae radix* extract;
75 mg *Achyranthis radix* extract;
75 mg *Corni officinalis* extract;
75 mg *Paeonis suffruticosa* extract;
75 mg *Alisma rhizoma* extract;
75 mg *Dioscorea villosa rhizoma* extract;
75 mg *Plantaginis semen* extract;
75 mg *hoelen* extract;
25 mg cinnamon cortex extract; and
5 mg *Piper nigrum* extract.

* * * * *